United States Patent
Siddalingappa

(10) Patent No.: US 11,793,748 B1
(45) Date of Patent: Oct. 24, 2023

(54) PHARMACEUTICAL COMPOSITIONS OF ASPIRIN FOR PARENTERAL ADMINISTRATION

(71) Applicant: GOOD HEALTH, LLC, Princeton, NJ (US)

(72) Inventor: Basavaraj Siddalingappa, Gujarat (IN)

(73) Assignee: GOOD HEALTH, LLC, Princeton, NJ (US)

( * ) Notice: Subject to any disclaimer, the term of this patent is extended or adjusted under 35 U.S.C. 154(b) by 0 days.

(21) Appl. No.: 16/840,095

(22) Filed: Apr. 3, 2020

Related U.S. Application Data

(60) Provisional application No. 62/830,024, filed on Apr. 5, 2019.

(51) Int. Cl.

| | |
|---|---|
| A61K 9/00 | (2006.01) |
| A61K 31/616 | (2006.01) |
| A61K 9/16 | (2006.01) |
| A61K 47/26 | (2006.01) |
| A61K 47/12 | (2006.01) |
| A61K 9/08 | (2006.01) |

(52) U.S. Cl.
CPC .......... *A61K 9/0019* (2013.01); *A61K 9/1623* (2013.01); *A61K 9/1635* (2013.01); *A61K 31/616* (2013.01); *A61K 47/12* (2013.01); *A61K 47/26* (2013.01); *A61K 9/08* (2013.01)

(58) Field of Classification Search
CPC .. A61K 9/0019; A61K 31/616; A61K 9/1623; A61K 47/26; A61K 47/12; A61K 9/1635; A61K 9/08
See application file for complete search history.

(56) References Cited

U.S. PATENT DOCUMENTS

| | | | | |
|---|---|---|---|---|
| 4,748,174 A | * | 5/1988 | Veronesi | C07C 59/68 562/460 |
| 5,028,625 A | * | 7/1991 | Motola | A61K 31/19 514/642 |
| 5,723,453 A | | 3/1998 | Phykitt | |
| 8,460,640 B2 | * | 6/2013 | Vinson | A61P 25/36 424/10.1 |
| 8,481,600 B2 | | 7/2013 | Somberg et al. | |
| 9,072,661 B2 | | 7/2015 | Pavliv et al. | |
| 2010/0173875 A1 | | 7/2010 | Somberg et al. | |

FOREIGN PATENT DOCUMENTS

| | | |
|---|---|---|
| CN | 1739530 A | 3/2006 |
| WO | 87/05010 A1 | 8/1987 |
| WO | 00/02565 A1 | 1/2000 |
| WO | WO 2007/129961 | * 11/2007 |
| WO | WO 2013/138628 | * 9/2013 |
| WO | 2018/222583 A1 | 12/2018 |

OTHER PUBLICATIONS

Patel et al., "Formulation, development and evaluation of injectable formulation of Aspirin", Drugs and Therapy Studies, 2013; vol. 3:e2.
Brain et al., "Onset of Analgesia and Efficacy of Ibuprofen Sodium in Postsurgical Dental Pain A Randomized, Placebo-controlled Study Versus Standard Ibuprofen," Clin. J. Pain 31(5):444-450 (2015).
De Paiva Lacerda et al., "Liquid anti-solvent recrystallization to enhance dissolution of CRS 74, a new antiretroviral drug," Drug Dev. Ind. Pharm. 41(11):1910-1920 (2015).
Fersht et al., "The Hydrolysis of Aspirin. Intramolecular General Base Catalysis of Ester Hydrolysis," J. Am. Chem. Soc. 89(19):4857-4863 (1967).
Ibuprofen 400 mg Solution for Infusion (located at: https://www.medicines.org.uk/emc/product/12036/smpc#gref).
Javadzadeh et al., "Recrystallization of Drugs—Effect on Dissolution Rate," Recrystallization in Materials Processing pp. 191-211 (2015).
Nowee et al., "Antisolvent crystallization: Model identification, experimental validation and dynamic simulation," Chem. Eng. Sci. 63(22):5457-5467 (2008).
Preskar et al., "Solubilization of ibuprofen for freeze dried parenteral dosage forms," Acta Pharm. 69(1):17-32 (2019).

* cited by examiner

*Primary Examiner* — Shirley V Gembeh
(74) *Attorney, Agent, or Firm* — RAPHAEL BELLUM PLLC

(57) ABSTRACT

The invention relates to methods for the parenteral administration of aspirin, pharmaceutical compositions of aspirin prepared using the methods, and kits that may be used in the method. The method of the invention comprises the steps of: mixing a first vial comprising aspirin and optionally at least one excipient with a second vial comprising an aqueous solution comprising meglumine, sodium citrate, or mixtures thereof, optionally at least one surfactant, tonicity adjusting agent, or mixtures thereof, optionally at least one monosaccharide, disaccharide, sugar alcohol, or mixtures thereof, and optionally at least one non-aqueous co-solvent; to obtain an aqueous aspirin composition; and parenterally administering the aqueous aspirin composition to the subject in need thereof.

23 Claims, No Drawings

PHARMACEUTICAL COMPOSITIONS OF ASPIRIN FOR PARENTERAL ADMINISTRATION

CROSS-REFERENCE TO RELATED APPLICATIONS

This application claims priority to U.S. Provisional Application No. 62/830,024, filed Apr. 5, 2019, the disclosure of which is incorporated herein by reference.

FIELD OF THE INVENTION

The invention relates to methods for the parenteral administration of aspirin, pharmaceutical compositions of aspirin prepared by the methods, and kits that may be used in the method.

BACKGROUND OF THE INVENTION

The poor solubility and instability of drugs in physiological acceptable diluents/vehicles recommended for injectable preparations is a major concern for the development of viable injectable preparations.

Aspirin is poorly soluble in water with a solubility of 3 mg/mL at 25° C., and prolonged agitation is usually required in order to dissolve the aspirin. However, degradation of the aspirin happens at the same time as the solubilization due to the required longer agitation times (Sigma Aldrich Product Information and U.S. Pat. No. 5,723,453 A).

Aspirin is reported to be soluble in aqueous alkali hydroxide solutions and aqueous bicarbonate solutions. However, the solubilization is accompanied by aspirin degradation.

Several attempts were made to prepare soluble forms of aspirin, most of those involved the preparation of soluble salts of aspirin, mainly sodium (WO 2000/002565 A1; WO 1987/005010 A1) and lysine (CN 1739530 A). Most of the salts, however, were found to be hygroscopic and unstable. The complicated process of preparing the aspirin salts, their hygroscopic nature, and their instability present major issues.

U.S. Pat. No. 8,481,600 B2 discloses parenteral compositions of aspirin consisting of a co-solvent diluent containing dimethyl acetamide. However, the use of dimethyl acetamide in a parenteral composition is not highly desirable due to its leaching effect on certain types of injection sets.

U.S. Pat. No. 8,481,600 B2 also presents data on the solubility of aspirin in various aqueous buffers, including bicin, tricin, CAPS, TAPS, HEPES, and AMPSO buffers. However, the solubility of aspirin was poor in those solutions and remained as suspended particles.

Some injectable formulations of aspirin have also been disclosed by the preparation of a lyophilized cake of aspirin using solutions of aspirin with mixtures of various organic solvents and water in the presence of mannitol. The resulting lyophilized cakes were reconstituted with diluent containing 80% water and 20% PEG-400 (Patel et al., 2013. Formulation, development and evaluation of injectable formulation of Aspirin. *Drugs and Therapy Studies*, 3(1), p.2.)

WO 2018/222583 discloses parenteral formulations of aspirin, wherein sterile aspirin is present in one vial and diluent for reconstitution is present in another vial. Sterile aspirin was produced by freeze drying of the semi-aqueous solution with an alcohol solvent. The diluent contains a base and polysorbate-80.

U.S. Pat. No. 8,481,600 B2 and WO 2018/222583 disclose the use of polysorbates for improving dissolution of aspirin. However, use of polysorbates, such as various Tweens, in intravenous injections has been reported to cause hypersensitive reactions in patients, including bronchospasm and hypotension. Therefore, if possible, it is recommended to avoid Tweens and Cremophores in intravenous formulations.

Thus, there still exists a need for improved methods of administering aspirin parenterally. The invention provides a solution to this need.

SUMMARY OF THE INVENTION

The invention relates to a method for the parenteral administration of aspirin to a subject in need thereof, comprising, consisting essentially of, or consisting of the steps of:
mixing:
a first vial comprising, consisting essentially of, or consisting of:
aspirin; and
optionally at least one excipient; with
a second vial comprising, consisting essentially of, or consisting of an aqueous solution comprising, consisting essentially of, or consisting of:
meglumine, sodium citrate, or mixtures thereof;
optionally at least one surfactant, tonicity adjusting agent, or mixtures thereof;
optionally at least one monosaccharide, disaccharide, sugar alcohol, or mixtures thereof; and
optionally at least one non-aqueous co-solvent,
to obtain an aqueous aspirin composition; and
parenterally administering the aqueous aspirin composition to the subject in need thereof.

The invention also relates to an aqueous aspirin composition prepared by mixing the first and second vials of the method of the invention.

The invention further relates to a kit for the parenteral administration of aspirin, comprising, consisting essentially of, or consisting of the first and second vials of the method of the invention.

DETAILED DESCRIPTION OF THE INVENTION

The invention relates to a method for the parenteral administration of aspirin to a subject in need thereof, comprising, consisting essentially of, or consisting of the steps of:
mixing:
a first vial comprising, consisting essentially of, or consisting of:
aspirin; and
optionally at least one excipient; with
a second vial comprising, consisting essentially of, or consisting of an aqueous solution comprising, consisting essentially of, or consisting of:
meglumine, sodium citrate, or mixtures thereof;
optionally at least one surfactant, tonicity adjusting agent, or mixtures thereof;
optionally at least one monosaccharide, disaccharide, sugar alcohol, or mixtures thereof; and
optionally at least one non-aqueous co-solvent,
to obtain an aqueous aspirin composition; and
parenterally administering the aqueous aspirin composition to the subject in need thereof.

Preferably, the aspirin present in the first vial is micronized. For example, the aspirin may have a particle size of D90<200 µm, preferably D90<150 µm, more preferably D90<100 µm, even more preferably D90<50 µm. The aspirin is present an amount ranging from about 10-1000 mg/vial, preferably about 50-750 mg/vial Preferably, the aspirin is sterilized and can be produced through various techniques, such as sterile recrystallization, terminal sterilization technique, including autoclaving with low temperature cycle, gamma irradiation, UV light exposure, or any other appropriate technique. The aspirin can be prepared using any generally well-known pharmaceutical milling techniques, such as cutting, attrition, impact, compression, controlled crystallization, spray drying, or any other appropriate process.

The excipients in the first vial may be present in an amount ranging from about 50-1000 mg, preferably 75-500 mg, and may be selected from the group consisting of sugars (e.g., glucose, fructose, galactose, mannitol, sucrose, lactose, trehalose, maltose), sugar derivatives, polyvinyl pyrrolidones, inorganic salts, and mixtures thereof.

The meglumine, sodium citrate, or mixtures thereof in the second vial are present in an amount ranging from about 10-1000 mg/mL, preferably about 20-500 mg/mL, more preferably about 30-200 mg/mL, even more preferably about 40-150 mg/mL. The sodium citrate may be monosodium citrate, disodium citrate, or trisodium citrate. Preferably, the sodium citrate is trisodium citrate.

The surfactant, tonicity adjusting agent, or mixtures thereof in the second vial may be present in an amount ranging from about 0.0001-10% w/v, such as about 0.001-8% w/v, such as about 0.01 to 5% w/v, such as about 0.1-2% w/v. Preferably, the surfactant is selected from the group consisting of fatty acid esters, block copolymers, and mixtures thereof, such as, for example, polysorbates (e.g., Tween-80, Polysorbate-80), cremophores (e.g., Cremophore EL), and poloxamers (e.g., Poloxamer-188). Preferably, the tonicity adjusting agent is selected from the group consisting of sodium chloride, dextrose, and mixtures thereof.

The monosaccharide, disaccharide, sugar alcohol, or mixtures thereof in the second vial may be present in an amount ranging from about 50-2000, such as 100-1000 mg, such as 250-750 mg, and may be selected from the group consisting of glucose, fructose, galactose, mannitol, sucrose, lactose, trehalose, maltose, and mixtures thereof. The monosaccharide, disaccharide, sugar alcohol, or mixtures thereof may also be present as an excipient in the first vial.

The non-aqueous co-solvent in the second vial may be present in an amount ranging from about 0.001-99% v/v, preferably about 0.1-90% v/v, more preferably about 1-85% v/v, even more preferably about 10-80% v/v, even more preferably about 20-60% v/v, most preferably about 30-50% v/v. Exemplary non-aqueous co-solvents include propylene glycol, ethanol, polyethylene glycols (e.g., PEG 200, PEG 300, PEG 400, PEG 500, PEG 600), or mixtures thereof.

The second vial may further contain at least one additional basifying agent, alkalizing agent, and/or pH modifying agent, including, for example, alkali hydroxide, alkali carbonates, alkali metal salts, aminoacids, aminosugars, and mixtures thereof. For example, the second vial may further contain arginine, lysine, tromethamine, sodium bicarbonate, and mixtures thereof.

In some aspects, the first and/or second vials do not contain an excipient, a non-aqueous co-solvent, a surfactant, and/or a tonicity adjusting agent.

The pH of the aqueous aspirin composition is in the range of about 3-7, preferably about 4-6. Upon mixing the first and second vials, the aspirin may be reconstituted in the aqueous solution in less than about 5 minutes, preferably less than about 4 minutes, more preferably less than about 3 minutes, and even more preferably less than about 2 minutes. After mixing the first and second vials, the aqueous aspirin composition may not contain solid aspirin particulate.

Less than about 5% of the aspirin in the aqueous aspirin composition will degrade to degradation products, such as salicylic acid, after 5 hours at about 2-8° C. during storage.

The aqueous aspirin composition is suitable for parenteral administration to a subject in need thereof, such as intravenous injection, intramuscular injection, intraperitoneal injection, or subcutaneous injection. As used herein, the term "subject" means a mammal, such as a human. The aqueous aspirin composition may be administered to subjects in need of aspirin therapy, such as emergency situations involving myocardial infarction.

The invention also relates to an aqueous aspirin composition prepared by mixing a first vial and a second vial,
  wherein the first vial comprises, consists essentially of, or consists of:
    aspirin; and
    optionally at least one excipient; with
  wherein the second vial comprises, consists essentially of, or consists of an aqueous solution comprising, consisting essentially of, or consisting of:
    meglumine, sodium citrate, or mixtures thereof;
    optionally at least one surfactant, tonicity adjusting agent, or mixtures thereof;
    optionally at least one monosaccharide, disaccharide, sugar alcohol, or mixtures thereof; and
    optionally at least one non-aqueous co-solvent.

The invention further relates to a kit for the parenteral administration of aspirin, comprising, consisting essentially of, or consisting of a first vial and a second vial,
  wherein the first vial comprises, consists essentially of, or consists of:
    aspirin; and
    optionally at least one excipient; with
  wherein the second vial comprises, consists essentially of, or consists of an aqueous solution comprising, consisting essentially of, or consisting of:
    meglumine, sodium citrate, or mixtures thereof;
    optionally at least one surfactant, tonicity adjusting agent, or mixtures thereof;
    optionally at least one monosaccharide, disaccharide, sugar alcohol, or mixtures thereof; and
    optionally at least one non-aqueous co-solvent.

As used herein, the term "vial" includes vials and any other container appropriate for holding the contents described herein, such as ampoules.

EXAMPLES

Example 1

Solubility Testing of Aspirin in Commonly Used Co-Solvents

The solubility of aspirin was determined using propylene glycol and polyethylene glycol (PEG-300 and PEG-400), which are widely used in intravenous formulations. See Table 1.

TABLE 1

Solubility of aspirin in co-solvents

| Solvent | Reconstitution time for unmilled Aspirin | Reconstitution time for milled API (Approx. 124 μm, BSS Sieve 120 passed) |
|---|---|---|
| Propylene glycol | 120 mg/3 mL Not easily soluble, needs sonication | 120 mg/3 mL Soluble in 3 minutes, after shaking. |
| PEG-300 | 120 mg/3 mL Not easily soluble, needs sonication | 120 mg/3 mL Soluble in 3 minutes, after shaking. |
| PEG-400 | 120 mg/3 mL Not easily soluble, needs sonication | 120 mg/3 mL Soluble in 3 minutes, after shaking. |

Table 1 indicates that the solubilization of aspirin in solvents takes longer if the aspirin is not milled.

Example 2

Effect of Bases on Reconstitution Time For Aspirin in Propylene Glycol

Solutions of propylene glycol with different bases were prepared by sonicating mixtures of propylene glycol and bases. See Table 2. Aspirin was added to those solutions and shaken in a circular motion.

TABLE 2

Effect of bases on reconstitution time for aspirin in propylene glycol

| Solvent | Amount of Aspirin | Reconstitution time for milled API (Approx. 124 μm, BSS Sieve 120 passed) |
|---|---|---|
| Propylene glycol with 10 mg/mL Arginine | 40 mg/mL | Reconstitution time 3 minutes with shaking. |
| Propylene glycol with 10 mg/mL Lysine | 40 mg/mL | Reconstitution time 1.40 minutes with shaking. |
| Propylene glycol with 10 mg/mL Meglumine | 40 mg/mL | Reconstitution time 2 minutes with shaking. |
| Propylene glycol with 10 mg/mL Tromethamine | 40 mg/mL | Reconstitution time 1.45 minutes with shaking. |

Table 2 suggests that among the basifiers tested lysine, meglumine, and tromethamine (Tris) are better in aiding solubilization.

Example 3

Solubility and Reconstitution Time For Aspirin in Semi-Aqueous Diluents

Diluent solutions were prepared by mixing solvent and water. See Table 3. Aspirin was added and the vials were shaken in a swirling motion.

TABLE 3

Solubility of aspirin in semi-aqueous diluents

| Solvent | aspirin (Sieve 120 mesh passed) | Amount of co-solvent | Water | Observation |
|---|---|---|---|---|
| Propylene glycol | 80 mg | 1.8 mL | 1.2 mL | Turbid with particles even after shaking for 5 minutes. |
| PEG 300 | 80 mg | 1.8 mL | 1.2 mL | Turbid with particles even after shaking for 5 minutes. |
| PEG 400 | 80 mg | 1.8 mL | 1.2 mL | Turbid with particles even after shaking for 5 minutes. |

Table 3 indicates that aspirin is not readily soluble in water rich water-solvent mixtures. Something additional is needed to solubilize aspirin quickly.

Example 4

Effect of Sugars on Solubilization of Aspirin in Solvent-Water Mixture

Diluent Preparation: Water, lactose, and base were taken in a vial and sonicated until a clear solution is formed. See Table 4. Solvent was then added and mixed for a minute.

To these diluents, aspirin was added and shaken in a swirling motion.

TABLE 4

Effect of lactose on reconstitution time

| Drug | Base | Lactose | Solvent (Water + Co-Solvent) | Reconstitution time | Observation |
|---|---|---|---|---|---|
| Co-solvent: PEG 300 | | | | | |
| Aspirin 80 mg | Tris 40 mg | 80 mg | 1.8 ml + 1.2 ml | 3.20 min | Clear |
| Aspirin 80 mg | Lysine 40 mg | 80 mg | 1.8 ml + 1.2 ml | 3.15 min | Clear |
| Co-solvent: PEG 400 | | | | | |
| Aspirin 80 mg | Tris 40 mg | 80 mg | 1.8 ml + 1.2 ml | 2.40 min | Clear |
| Aspirin 80 mg | Lysine 40 mg | 80 mg | 1.8 ml + 1.2 ml | 3.50 min | Clear |

Table 4 demonstrates that inclusion of lactose in diluents made of basified solutions of water-solvent mixtures resulted in improved dissolution and reconstitution time for aspirin.

Example 5

Effect of Combination of Lactose and Mannitol on Solubility and Reconstitution Time For Aspirin A mixture of lactose and mannitol were tried to improve reconstitution time. See Tables 5 and 6.

TABLE 5

Reconstitution time for diluents containing 80 mg each of lactose and mannitol

| Drug | Base | Lactose + Mannitol (50:50) | Solvent (Water + PEG-300) | Reconstitution time | Observation |
|---|---|---|---|---|---|
| Aspirin 80 mg (120 sieve passed) | Tris 40 mg | 80 mg + 80 mg | 1.8 ml + 1.2 ml | 2.10 min | Clear |

TABLE 5-continued

Reconstitution time for diluents containing 80 mg each of lactose and mannitol

| Drug | Base | Lactose + Mannitol (50:50) | Solvent (Water + PEG-300) | Reconstitution time | Observation |
|---|---|---|---|---|---|
| Aspirin 80 mg (120 sieve passed) | Tris 40 mg | 80 mg + 80 mg | 1.5 ml + 1.5 ml | 2.25 min | Clear |
| Aspirin 80 mg (120 sieve passed) | Tris 40 mg | 80 mg + 80 mg | 1.2 ml + 1.8 ml | 2.10 min | Slightly hazy |
| Aspirin 80 mg (120 sieve passed) | Lysine 40 mg | 80 mg + 80 mg | 1.2 ml + 1.8 ml | 2.00 min | Slightly hazy |

Diluents were then prepared by dissolving base and sugars in water and followed by addition of PEG 300. The diluent was transferred to a vial containing aspirin, and the vial was shaken in a swirling motion.

TABLE 6

Reconstitution time for diluents containing 20 mg lactose and 60 mg mannitol

| Drug | Base | Lactose + Mannitol (25:75) | Solvent (Distilled water + PEG 300) | Reconstitution time | Observation |
|---|---|---|---|---|---|
| Aspirin 80 mg (120 sieve passed) | Tris 40 mg | 20 mg + 60 mg | 1.8 ml + 1.2 ml | 2.30 min | Clear |
| Aspirin 80 mg (120 sieve passed) | Meglumine 40 mg | 20 mg + 60 mg | 1.8 ml + 1.2 ml | 2.30 min | Clear |
| Aspirin 80 mg (120 sieve passed) | Tris 40 mg | 20 mg + 60 mg | 1.5 ml + 1.5 ml | 2.10 min | Clear |
| Aspirin 80 mg (120 sieve passed) | Meglumine 40 mg | 20 mg + 60 mg | 1.5 ml + 1.5 ml | 2.20 min | Clear |
| Aspirin 80 mg (120 sieve passed) | Tris 40 mg | 20 mg + 60 mg | 1.2 ml + 1.8 ml | 2.00 min | Clear |
| Aspirin 80 mg (120 sieve passed) | Meglumine 40 mg | 20 mg + 60 mg | 1.2 ml + 1.8 ml | 2.00 min | Slightly hazy |

As shown in Tables 5 and 6, lactose and mannitol used together further improve reconstitution time.

Example 6

Effect Pre-Mixing of Aspirin with Lactose on Reconstitution Time

Diluents were prepared by dissolving base in water and followed by addition of PEG 300. See Tables 7. The diluent was transferred to a vial containing aspirin triturated with lactose. The mixture was shaken in the vial in a swirling motion.

TABLE 7

Reconstitution time for aspirin-lactose premix

| Drug | Base | Solvent (Water + Propylene glycol) | Reconstitution time | Observation |
|---|---|---|---|---|
| Aspirin 80 mg + 160 mg lactose (both 120 sieve passed) | Tris 30 mg | 1.5 ml + 1.5 ml | 2.00 min | Clear |
| Aspirin 80 mg + 160 mg lactose (both 120 sieve passed) | Tris 35 mg | 1.5 ml + 1.5 ml | 1.25 min | Clear |
| Aspirin 80 mg + 160 mg lactose (both 120 sieve passed) | Tris 40 mg | 1.5 ml + 1.5 ml | 1.00 min | Clear |
| Aspirin 80 mg + 160 mg lactose (both 120 sieve passed) | Tris 50 mg | 1.5 ml + 1.5 ml | 1.40 min | Light hazy |

Table 7 indicates that lactose and aspirin premixing with lactose by trituration further improved reconstitution time.

Example 7

Additional Trials with Bicarbonates and Salts

Diluent was prepared by dissolving salt or base in water and PEG 300 was added to the mixtures to get clear solutions. See Table 8. The diluents were then added to sealed vials containing aspirin via a syringe and needle, and then shaken vigorously up and down for about 3 minutes.

TABLE 8

Reconstitution trials for micronized aspirin with semi-aqueous solutions containing bases

| Trial | Drug | Base | Solvent | Observation | pH of Reconstituted solutions |
|---|---|---|---|---|---|
| 1 | Aspirin 300 mg (120 sieve passed) | Sodium citrate 220 mg | 5 mL PEG 300 + 5 mL Water | Clear solution after 2-3 minutes shaking. | 5.35 |
| 2 | Aspirin 300 mg (120 sieve passed) | Sodium Bicarbonate 120 mg | 4 mL PEG 300 + 6 mL Water | Clear solution after 2-3 minutes shaking. | 5.42 |

Stability was determined by HPLC analysis using the following parameters:

Mobile Phase: Solution containing 15% acetonitrile and 85% water with 2 g/L of heptanesulfonate sodium. The pH of the solution was adjusted to 3.4.

Column: 250×4.6, 5 µ, C18

Flow rate: 2 mL/minute

Detection: 280 nm

Injection volume: 10 µl, the concentration of aspirin in sample and standard injections were maintained at about 0.5 mg/mL.

The solutions after reconstitution were clear and the pH of the solutions were acceptable. Table 9 provides the results of the stability of solutions after reconstitution.

TABLE 9

The stability data of Trial-1 and Trial-2

| | Trial-1 | | Trial-2 | |
|---|---|---|---|---|
| Time | Aspirin peak purity | % Salicylic acid | Aspirin peak purity | % Salicylic acid |
| Initial | 99.27 | 0.73 | 99.28 | 0.72 |
| 1 hour at room temperature | 96.54 | 3.46 | 96.95 | 3.05 |
| 2 hour at 2-8° C. | 98.64 | 1.36 | 98.27 | 1.73 |
| Aspirin API | 99.76% and 0.24% salicylic acid | | | |

The solutions of Trial-1 and Trial-2 have acceptable stability at 2-8° C. The solutions after reconstitution should be used immediately or should be stored in refrigerator.

Example 8

Reconstitution Trials with Aqueous Media Containing Only Bases or Alkalizers The bases or alkali salts were dissolved in 10 mL water. See Table 10. These solutions were transferred to 20 mL vials containing 300 mg milled aspirin. Shaken up and down vigorously to check reconstitution and clarity.

TABLE 10

Reconstitution trials for micronized Aspirin with aqueous solutions containing bases

| Trials | Drug | Base | Observations | pH of solutions |
|---|---|---|---|---|
| Trial-3 | Aspirin 300 mg passed through 120 mesh sieve | Sodium bicarbonate 300 mg in 10 mL water | Solution hazy | 7.22 |
| Trial-4 | Aspirin 300 mg passed through 120 mesh sieve | Tri-Sodium Citrate 300 mg in 10 mL water | Clear after shaking for 3-4 minutes | 4.31 |
| Trial-5 | Aspirin 300 mg passed through 120 mesh sieve | Meglumine 300 mg in 10 mL water | Clear after shaking for about 2 minutes | 4.47 |
| Trial-6 | Aspirin 300 mg passed through 120 mesh sieve | Tromethamine 300 mg in 10 mL water | Solution slightly hazy | Not measured |
| Trial-7 | Aspirin 300 mg passed through 120 mesh sieve | Lysine 300 mg in 10 mL water | Solution hazy | Not measured |

The stability of Trials 3-5 was tested using the HPLC method described above. See Table 11.

TABLE 11

Stability data for formulations of Trials 3-5

| | Trial-3 | | Trial-4 | | Trial-5 | |
|---|---|---|---|---|---|---|
| Time | Aspirin peak purity | % Salicylic acid | Aspirin peak purity | % Salicylic acid | Aspirin peak purity | % Salicylic acid |
| Initial | 99.36 | 0.64 | 99.36 | 0.64 | 99.28 | 0.72 |
| 1 hour at room temperature | 96.69 | 3.31 | 97.54 | 2.46 | 97.59 | 2.41 |
| 2 hour at 2-8° C. | 98.99 | 1.01 | 98.78 | 1.22 | 98.67 | 1.33 |
| Aspirin API | 99.76% and 0.24% salicylic acid | | | | | |

The reconstitution of higher doses of aspirin with aqueous solutions of bases indicate superiority using a combination of meglumine and sodium citrate over same bases used separately. See Table 12.

TABLE 12

Reconstitution trials for micronized aspirin higher concentrations (50 mg/mL) with aqueous solutions of bases

| Trials | Drug | Base | Observations | pH of solutions |
|---|---|---|---|---|
| Trial-8 | Aspirin 500 mg passed through 120 mesh sieve | Sodium bicarbonate 700 mg in 10 mL water | Solution slightly hazy | Not Measured |
| Trial-9 | Aspirin 500 mg passed through 120 mesh sieve | Tri-Sodium Citrate 700 mg in 10 mL water | Solution very slightly hazy | Not Measured |
| Trial-10 | Aspirin 500 mg passed through 120 mesh sieve | Meglumine 700 mg in 10 mL water | Solution very slightly hazy | Not Measured |
| Trial-11 | Aspirin 500 mg passed through 120 mesh sieve | Meglumine 400 + Trisodium citrate 300 mg in 10 mL water | Clear after shaking for about 2-3 minutes | 5.38 |

Aspirin at higher concentration with aqueous solution containing both meglumine and sodium citrate was stable for a period of about 5 hours at 2-8° C. See Table 13.

TABLE 13

Stability data for Trial-11, reconstituted solution of Aspirin (50 mg/mL)

| | Trial-11 | |
|---|---|---|
| Time | Aspirin peak purity | % Salicylic acid |
| Initial | 99.14 | 0.86 |
| 1 hour at room temperature | 96.69 | 3.31 |
| 2 hour at 2-8° C. | 98.5 | 1.5 |
| 5 hour at 2-8° C. | 97.99 | 2.01 |

The reconstitution of lower concentrations of aspirin (5.0 mg/mL) with aqueous solutions of bases indicated that reconstitution of aspirin with meglumine resulted in a clear solution within about 2 minutes. See Table 14. Therefore, these dilute solutions of the invention are suitable for slow infusion for a longer time. For example, the infusion can be made over 30 minutes to about 100 minutes with an infusion rate of about 3 mL/min to 0.8 mL/min. The rate of infusion of the invention can depend on the clinical conditions of patients, and can be modified as necessary. In certain cases, a bolus injection of concentrated aspirin solutions may be required. The aspirin solution (50 mg/mL) of the invention can be given as a bolus injection (e.g., 10 mL within 2-5 minutes).

TABLE 14

Reconstitution trials for micronized aspirin lower concentrations (5 mg/mL) with aqueous solutions of bases

| Trials | Drug | Base | Observations | pH of solutions |
|---|---|---|---|---|
| Trial-12 | Aspirin 50.0 mg passed through 120 mesh sieve | Meglumine 54 mg in 10 mL saline | Solution was clear in less than 2 minutes after shaking. | 6.24 |

TABLE 14-continued

Reconstitution trials for micronized aspirin lower concentrations (5 mg/mL) with aqueous solutions of bases

| Trials | Drug | Base | Observations | pH of solutions |
|---|---|---|---|---|
| Trial-13 | Aspirin 50.0 mg passed through 120 mesh sieve | Meglumine 55 mg in 10 mL saline | Solution was clear in less than 2 minutes after shaking. | 7.6 |
| Trial-14 | Aspirin 50.0 mg passed through 120 mesh sieve | Meglumine 54 mg in 10 mL 5% W/V dextrose | Solution was clear in less than 2 minutes after shaking. | 5.68 |
| Trial-15 | Aspirin 50.0 mg passed through 120 mesh sieve | Meglumine 55 mg in 10 mL 5% W/V dextrose | Solution was clear in less than 2 minutes after shaking. | 5.64 |
| Trial-16 | Aspirin 50.0 mg passed through 120 mesh sieve | Meglumine 10 mg, Trisodium citrate 80 mg in 10 mL 5% W/V dextrose | Solution was clear in less than 2 minutes after shaking. | 5.44 |
| Trial-17 | Aspirin 50.0 mg passed through 120 mesh sieve | Meglumine 10 mg, Trisodium citrate 80 mg in 10 mL saline | Solution was clear in less than 2 minutes after shaking. | 5.21 |

The stability of aspirin at lower concentration with aqueous solution at room temperature and refrigerated conditions (2-8° C.) indicated that the dilute solutions with only meglumine were more stable with tonicity adjuster dextrose compared to sodium chloride. See Tables 15 and 16. With a mixture of meglumine and sodium citrate, the aspirin was equally stable with dextrose and sodium chloride.

TABLE 15

Stability data of dilute aspirin solutions (Room temperature)

| | Initial | | 1 hour | | 2 hour | |
|---|---|---|---|---|---|---|
| Formulations | % Assay | % S.A | % Assay | % S.A | % Assay | % S.A |
| Trial-12 | 97.27 | 0.35 | 96.76 | 3.35 | 96.18 | 5.59 |
| Trial-13 | 98.72 | 0.36 | 98.18 | 3 | 97.43 | 5.5 |
| Trial-14 | 94.01 | 0.39 | 93.8 | 2.82 | 92.25 | 4.52 |
| Trial-15 | 97.26 | 0.44 | 96.94 | 2.71 | 86.77 | 5.48 |
| Trial-16 | 103.39 | 0.2 | 103.02 | 2.42 | 99.03 | 4.37 |
| Trial-17 | 103.63 | 0.28 | 102.09 | 2.19 | 99.97 | 4.11 |

Note:
S.A is salicylic acid impurity

TABLE 16

Stability data of dilute aspirin solutions (Refrigerator, 2-8° C.)

| | Initial | | 2 hour | | 8 hour | |
|---|---|---|---|---|---|---|
| Formulations | % Assay | % S.A | % Assay | % S.A | % Assay | % S.A |
| Trial-12 | 95.52 | 0.39 | 95.46 | 0.64 | 93.53 | 1.02 |
| Trial-13 | 93.13 | 0.39 | 93.5 | 0.64 | 93.48 | 1.05 |
| Trial-14 | 94.46 | 0.3 | 92.96 | 0.88 | 93.23 | 1.27 |
| Trial-15 | 94.4 | 0.28 | 92.35 | 0.79 | 96.07 | 1.28 |
| Trial-16 | 101.78 | 0.32 | 99.06 | 0.86 | 100.28 | 1.35 |
| Trial-17 | 104.61 | 0.25 | 102.01 | 0.79 | 103.98 | 1.42 |

Note:
S.A is salicylic acid impurity

Overall, dilute isotonic solutions of aspirin can be made with either meglumine alone or with meglumine-sodium citrate along with isotonicity adjusting excipients. Since aspirin hydrolyzes quickly in the blood to give salicylic acid, it is preferable to use dilute solutions for longer infusion to maintain the aspirin for a longer time in the blood. See, e.g., Nagelschmitz et al., "Pharmacokinetics and pharmacodynamics of acetylsalicylic acid after intravenous and oral administration to healthy volunteers," *Clinical Pharmacology: Advances and Applications* 6(1):51-59 (2014).

Example 9

Stability of Recrystallized Aspirin Powder

Recrystallization of aspirin powder in different solvents was performed as indicated in Scheme 1 below.

Scheme 1

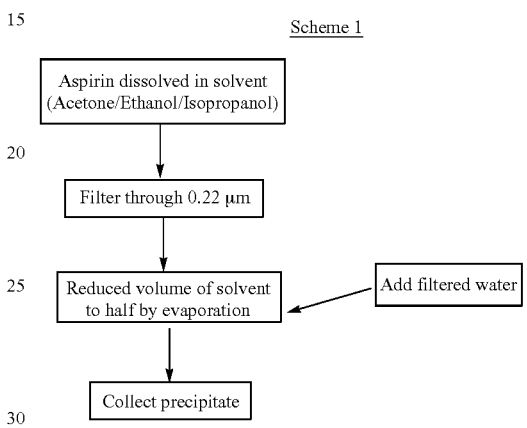

Aspirin recrystallized from acetone, ethanol, and isopropanol was stable at accelerated conditions. See Table 17. This indicates that aspirin is stable at room temperature for at least 2 years. Therefore, sterile aspirin can be manufactured by recrystallization/filtration. Such recrystallized aspirin is stable, and recrystallization does not affect its stability.

TABLE 17

Stability data of recrystallized Aspirin powder

| | 6 months 40° C./75% RH | |
|---|---|---|
| API BATCHES | % Assay | % S.A |
| Recrystallization from Acetone | 97.20 | 0.505 |
| Recrystallization from Ethanol | 97.72 | 0.452 |
| Recrystallization from Isopropanol | 99.35 | — |

Note:
S.A is salicylic acid impurity

Surprisingly, reconstitution with aqueous bases, only meglumine and sodium citrate containing solutions resulted in completely clear solutions. However, sodium bicarbonate and other bases containing solutions resulted in hazy solutions. The reason for formation of clear solutions with just meglumine and trisodium citrate is unknown.

Overall, the inventors have unexpectedly demonstrated that fast reconstitution of aspirin with commonly used co-solvents is not possible; milling of aspirin results in faster reconstitution time; addition of bases or aminoacids results in faster reconstitution time; in mixtures of water-co-solvent-base, inclusion of sugars such as lactose, mannitol, or mixtures thereof, enhances dissolution and reduces reconstitution time; and in aqueous solutions containing bases/ alkali salts, reconstitution time is short and clear solutions are formed only with meglumine and sodium citrate, and meglumine has a relatively shorter reconstitution time.

What is claimed is:

1. A method for the parenteral administration of aspirin to a subject in need thereof, comprising the steps of:
mixing:
a first vial comprising:
non-lyophilized sterile aspirin in solid form; and
optionally at least one excipient; with
a second vial comprising an aqueous solution comprising:
meglumine and sodium citrate;
optionally at least one surfactant, tonicity adjusting agent, or mixtures thereof;
optionally at least one monosaccharide, disaccharide, sugar alcohol, or mixtures thereof; and
optionally at least one non-aqueous co-solvent,
to obtain a stable aqueous aspirin composition; and
parenterally administering the aqueous aspirin composition to the subject in need thereof.

2. The method of claim 1, wherein the aspirin is micronized.

3. The method of claim 1, wherein the aspirin has a particle size of D90<200 μm.

4. The method of claim 1, wherein the aspirin is present in an amount ranging from about 10-1000 mg/vial.

5. The method of claim 1, wherein the excipient is selected from the group consisting of sugars, sugar derivatives, polyvinyl pyrrolidones, inorganic salts, and mixtures thereof.

6. The method of claim 1, wherein the meglumine and sodium citrate are present in an amount ranging from about 10-1000 mg/mL.

7. The method of claim 1, wherein the surfactant, tonicity adjusting agent, or mixtures thereof is present in an amount ranging from about 0.0001-10% w/v.

8. The method of claim 1, wherein the surfactant is selected from the group consisting of fatty acid esters, block copolymers, and mixtures thereof.

9. The method of claim 1, wherein the surfactant is selected from the group consisting of polysorbates, cremophores, poloxamers, and mixtures thereof.

10. The method of claim 1, wherein the tonicity adjusting agent is selected from the group consisting of sodium chloride, dextrose, and mixtures thereof.

11. The method of claim 1, wherein the monosaccharide, disaccharide, sugar alcohol, or mixtures thereof is present in an amount ranging from about 50-2000 mg.

12. The method of claim 1, wherein the at least one non-aqueous co-solvent is present in an amount ranging from about 0.001-99% v/v.

13. The method of claim 1, wherein the at least one non-aqueous co-solvent is selected from the group consisting of propylene glycol, ethanol, polyethylene glycol, and mixtures thereof.

14. The method of claim 1, wherein the pH of the aqueous aspirin composition is in the range of about 3-7.

15. The method of claim 1, wherein the aspirin is reconstituted in the aqueous solution in less than about 5 minutes.

16. The method of claim 1, wherein the amount of aspirin degradation to salicylic acid in the aqueous aspirin composition after 5 hours at about 2-8° C. is less than about 5%.

17. The method of claim 1, wherein the parenteral administration is intravenous injection, intramuscular injection, intraperitoneal injection, or subcutaneous injection.

18. The method of claim 1, wherein the subject is a human.

19. The method of claim 1, wherein, prior to mixing the first vial and the second vial, the non-lyophilized aspirin in solid form in the first vial is sterilized by recrystallization.

20. The method of claim 1, wherein the non-lyophilized aspirin is micronized, has a particle size of D90<200 μm, and is present in an amount ranging from about 10-1000 mg/vial;
wherein the meglumine and sodium citrate are present in an amount ranging from about 10-1000 mg/mL.

21. The method of claim 1, wherein the sodium citrate is trisodium citrate.

22. A stable aqueous aspirin composition prepared by mixing a first vial and a second vial,
wherein the first vial comprises:
non-lyophilized sterile aspirin in solid form; and
optionally at least one excipient; with
wherein the second vial comprises an aqueous solution comprising:
meglumine and sodium citrate;
optionally at least one surfactant, tonicity adjusting agent, or mixtures thereof;
optionally at least one monosaccharide, disaccharide, sugar alcohol, or mixtures thereof; and
optionally at least one non-aqueous co-solvent.

23. A kit for the parenteral administration of a stable aqueous aspirin composition, comprising a first vial and a second vial,
wherein the first vial comprises:
non-lyophilized sterile aspirin in solid form; and
optionally at least one excipient; with
wherein the second vial comprises an aqueous solution comprising:
meglumine and sodium citrate;
optionally at least one surfactant, tonicity adjusting agent, or mixtures thereof;
optionally at least one monosaccharide, disaccharide, sugar alcohol, or mixtures thereof; and
optionally at least one non-aqueous co-solvent.

* * * * *